United States Patent [19]
Schoonen et al.

[11] Patent Number: 6,152,364
[45] Date of Patent: *Nov. 28, 2000

[54] MEDICAMENT DISTRIBUTION SYSTEM AND AUTOMATIC DISPENSER FOR SUCH SYSTEM

[75] Inventors: Adelbert Jozef Schoonen, Groningen; Cornelis Wilhelmus Schaap, Nijmegen, both of Netherlands

[73] Assignees: Consumer Health Entrepreneurs B.V.; Medimaat B.V., both of Netherlands

[ * ] Notice: This patent issued on a continued prosecution application filed under 37 CFR 1.53(d), and is subject to the twenty year patent term provisions of 35 U.S.C. 154(a)(2).

[21] Appl. No.: 08/750,354
[22] PCT Filed: Jun. 9, 1995
[86] PCT No.: PCT/NL95/00204
§ 371 Date: Feb. 6, 1997
§ 102(e) Date: Feb. 6, 1997
[87] PCT Pub. No.: WO95/25423
PCT Pub. Date: Sep. 28, 1995

[30] Foreign Application Priority Data

Jun. 9, 1994 [NL] Netherlands ............................ 9400941
Dec. 23, 1994 [NL] Netherlands ............................ 9402206

[51] Int. Cl.[7] .................................................. G06F 17/00
[52] U.S. Cl. ................................ 235/375; 235/385; 221/7
[58] Field of Search .................................... 235/375, 380, 235/381, 383, 385, 435, 454, 492, 493; 221/2, 7; 364/478, 479, 479.02, 479.07, 479.14

[56] References Cited

U.S. PATENT DOCUMENTS

| | | | |
|---|---|---|---|
| 3,491,870 | 1/1970 | Isserstedt . | |
| 3,780,907 | 12/1973 | Colburn et al. | 221/2 |
| 3,917,045 | 11/1975 | Williams et al. | 194/4 |
| 4,695,954 | 9/1987 | Rose et al. | 364/413 |
| 4,767,917 | 8/1988 | Ushikubo | 235/381 |
| 4,785,969 | 11/1988 | McLaughlin | 221/2 |
| 4,827,112 | 5/1989 | Yoshino et al. | 235/380 |
| 4,847,764 | 7/1989 | Halvorson | 364/413.2 |
| 4,953,745 | 9/1990 | Rowlett, Jr. | 221/5 |
| 5,208,762 | 5/1993 | Charhut et al. | 364/478 |
| 5,337,919 | 8/1994 | Spaulding et al. | 221/2 |
| 5,401,059 | 3/1995 | Ferrario | 283/67 |
| 5,451,760 | 9/1995 | Renvall | 235/462.01 |
| 5,511,594 | 4/1996 | Brennan et al. | 141/98 |

*Primary Examiner*—Michael G Lee
*Attorney, Agent, or Firm*—Rothwell, Figg, Ernst & Manbeck

[57] ABSTRACT

The invention relates to a pharmacy system for prescribing and delivering medicaments to a patient. The system includes at least one input unit with which a doctor is capable of entering, inter alia, a prescription of a medicament for a patient, together with the patient's identity, into the system. The input unit then generates a prescription signal corresponding to the prescription entered. A pharmacy computer coupled to the input unit further processes the prescription signal received from the input unit and generates a control signal corresponding to the prescription. Under the supply of the control signal generated by the pharmacy computer, an automatic dispenser dispenses the described medicament to the patient.

2 Claims, 2 Drawing Sheets

6,152,364

MEDICAMENT DISTRIBUTION SYSTEM AND AUTOMATIC DISPENSER FOR SUCH SYSTEM

BACKGROUND OF THE INVENTION

The invention relates to a pharmacy system for prescribing and delivering medicaments to a patient.

Distribution of medicaments prescribed by a doctor generally takes place via a pharmacy. It concerns a labor-intensive process which is carried out at least substantially manually. In this process, a doctor writes out a prescription on a sheet of paper with which a patient can then go to a pharmacy in order to collect the relevant medicament. However, written prescriptions are not always clear, which involves the risk that errors are made in the pharmacy. Also, the selection of medicaments (order picking) may give rise to errors being made.

The writing of a prescription belongs to the medical responsibility, while the pharmacist is by law charged with the duty of checking the prescription for unclarities and inaccuracies and to contact the doctor hereabout. For this reason, the total process of describing by the doctor and delivering by the pharmacist is generally carried out separately.

Accordingly, the law in for instance the Netherlands requires a separation between the prescribing and delivering of medicaments. Prescribing is reserved for the doctor and delivering is reserved for the pharmacist. From the prescription, the pharmacist carries out a number of checks, after which the medicaments are selected, labelled and delivered.

SUMMARY OF THE INVENTION

The invention inter alia relates to the automation of the delivery process, such that it will, moreover, still fall under the responsibility of a pharmacist. Accordingly, a pharmacy system according to the invention is characterized in that a possible embodiment of the pharmacy system for prescribing and delivering medicaments to a patient comprises at least one input unit with which a doctor is capable of entering inter alia a prescription of a medicament for a patient, together with the identity of the patient, into the system, the input unit generating a prescription signal corresponding to the prescription entered; a pharmacy computer coupled to the input unit, which pharmacy computer further processes the prescription signal received from the input unit and generates a control signal corresponding to the prescription; and at least one automatic dispenser which is suitable for being loaded with medicaments and which, under the supply of the control signal generated by the pharmacy computer, dispenses the medicaments prescribed.

The input unit may for instance be disposed in the consulting room of a doctor. The pharmacy computer, however, can then be disposed at and under the responsibility of a pharmacist. The automatic dispenser can for instance be disposed in or near the surgery of the prescribing doctor. This last means that the automatic dispenser and the pharmacy computer are spatially separated from each other. This involves a particularly great advantage of convenience to the patient. After all, after having consulted the doctor, the patient may directly take along the prescribed medicament, if any. Because the automatic dispenser is controlled by the pharmacy computer, the separation between pharmacist and doctor, as for instance required by the Dutch law, is maintained without change. In this respect, the automatic dispenser also falls under the responsibility of the pharmacist.

The filling of the automatic dispenser may also be carried out under the responsibility of the pharmacist.

The pharmacy system according to the invention also involves a substantial efficiency improvement. Owing to the automation of the delivery process, manual errors as described hereinabove can no longer occur. This considerably improves the quality of the delivery process. In addition, a considerable reduction of personnel costs is possible within the pharmacy, which involves an important economic advantage from which not only the pharmacist, but also the patient may profit.

In accordance with an advantageous embodiment of the invention, the pharmacy system further comprises means for determining the identity of a patient, the system comparing the identity determined with the identity of a patient associated with a prescription inputted. The effect thus achieved is that a medicament is always delivered to the right patient.

For this purpose, the system in particular comprises a number of patient cards, a patient card comprising the identity of a patient, and the automatic dispenser comprising a card reader for reading and accordingly determining the identity of a patient from the patient card. As a person should identify himself via the patient card, the identity of the holder of the card is known and, if so desired, a bill for the medicaments delivered can automatically be sent to the holder of the card by order of the pharmacist.

Preferably, the above-mentioned comparison is carried out by the pharmacy computer. This means that the matter is carried out directly under the responsibility of the pharmacist. However, the comparison can also be carried out by the automatic dispenser.

In accordance with a particular embodiment of the invention, the automatic dispenser comprises a control unit, a magazine capable of being filled with medicaments provided with an identification code, a selection unit with which medicaments can be selected from the magazine, and a code-reading unit capable of reading the identification code of a medicament, the control unit controlling, on the basis of the control signal received, the selection unit such that the medicament corresponding to the control signal is selected from the magazine, the code-reading unit reads the code of the selected medicament and transmits it to the control unit, whereupon the control unit determines on the basis of the code whether a medicament corresponding to the control signal has been selected. The check ensures that it is entirely impossible that a wrong medicament is delivered to a patient.

In particular, the selection unit conveys the selected medicament from the magazine. In accordance with another aspect of the invention, the selection unit releases the selected medicament to a patient when the control unit determines, on the basis of the identification code read, that a medicament corresponding to the control signal has been selected.

The automatic dispenser may further comprise a printer printing for instance the patient's name, the medicament and the dosage of the medicament on a label for the medicament to be released.

In accordance with a highly advanced embodiment of the invention, the input unit comprises a data bank wherein various data about indications with associated prescriptions of medicaments are stored, as well as for instance data of a patient, the input unit checking according to a predetermined algorithm whether a medicament prescribed for a patient corresponds to the data stored in the data bank. Hence, for drawing up the prescription, the doctor is assisted by the system. Also, unnecessary mistakes can be prevented. More in particular, the input unit issues a signal intended for the doctor when a deviation in the prescription is found during the check carried out by the input unit. In this connection, one may for instance think of the following deviations. The doctor selects a medicament which does not correspond to an indication entered by the doctor. The input unit may also generate a list of possible medicaments when an indication is entered, with the signal being produced when the doctor does not adopt the first choice of the input unit. Furthermore, a signal may be issued when not the usual strength or dosage of a medicament is inputted. In this manner, it is also possible to draw the doctor's attention to possible interactions with other medicaments prescribed.

In accordance with a particular embodiment of the invention, the prescription signal comprising a prescription having a deviation, also comprises information about the found deviation in the relevant prescription. This has as a great advantage that the pharmacist's attention can also been drawn to particular deviations in the prescription and that, if necessary, he may contact the doctor for consultation. For this purpose, the pharmacy computer produces for instance a signal intended for the pharmacist when a prescription signal having a found deviation is received.

In accordance with another important aspect of the invention, the pharmacy computer comprises a pharmacy data bank wherein various data about indications with associated prescriptions of medicaments are stored, as well as for instance patient data, the pharmacy computer checking according to a predetermined algorithm whether a prescription received by means of the prescription signal corresponds to the data stored in the pharmacy data bank. This means that an independent verification can be performed under the responsibility of the pharmacist. This verification may for instance comprise the same aspects as described with regard to the input unit. Here, too, the pharmacy computer may for instance produce a signal intended for a pharmacist when a deviation in the prescription is found during the verification performed by the pharmacy computer.

The invention also relates to an automatic dispenser suitable for use in a pharmacy system as described hereinabove.

By way of exception, for instance, in the Netherlands there are a number of dispensing general practitioners who provide the medicament distribution in thinly populated rural areas. This last involves a very heavy responsibility to the general practitioner. After all, the doctor should not only see to it that the correct medicament is prescribed, but also that the correct medicament is delivered to a patient.

Another object of the invention is to automate the delivery process at a dispensing general practitioner, in such a manner that the risk of wrong delivery of a medicament is minimized. Accordingly, an alternative embodiment of a pharmacy system according to the invention is characterized in that the pharmacy system comprises at least one input unit with which a doctor is inter alia capable of entering a prescription of a medicament for a patient together with the identity of a patient into the system, the input unit generating a prescription signal corresponding to the prescription entered, and at least one automatic dispenser coupled to the input unit to which automatic dispenser the prescription signal is supplied, the automatic dispenser, in service, being loaded with medicaments and delivering a prescribed medicament corresponding to the prescription signal.

The input unit may for instance be disposed in the consulting room of a doctor. The automatic dispenser may for instance be disposed in or near the surgery of the prescribing doctor. This last means that the automatic dispenser and the input unit can be spatially separated from each other. This involves a particularly great advantage of convenience to the patient. After all, after having consulted the doctor, the patient can directly take along the prescribed medicament, if any. The filling of the automatic dispenser can be carried out under the responsibility of a pharmacist as well as under the responsibility of the general practitioner.

The pharmacy system according to the invention also involves a substantial efficiency improvement. Owing to the automation of the delivery process, manual errors as described hereinabove can no longer occur. This considerably improves the quality of the delivery process. In addition, within the practice of the general practitioner, a considerable time saving is possible which involves an important economic advantage, from which not only the general practitioner, but also the patient may profit.

In accordance with an advantageous embodiment of the invention, the pharmacy system further comprises means for determining the identity of a patient, the system comparing the determined identity with the identity of a patient associated with a prescription entered and producing the above-mentioned prescription signal when these identities correspond to one each other. The effect thus achieved is that a medicament is always delivered to the right patient.

For this purpose, the system particularly comprises a number of patient cards, a patient card comprising the identity of a patient, and the automatic dispenser comprising a card reader for reading and accordingly determining the identity of a patient from the patient card. As a person should identify himself via the patient card, the identity of the holder of the card is known and, if so desired, a bill for the medicaments delivered can automatically be sent to the holder of the card by order of the general practitioner or pharmacist.

Preferably, the above-mentioned comparison is carried out by the input unit. This means that the matter is carried out directly under the responsibility of the general practitioner. However, it is also possible that this comparison is carried out by the automatic dispenser.

In accordance with a particular embodiment of the invention, the automatic dispenser comprises a control unit, a magazine capable of being filled with medicaments provided with an identification code, a selection unit with which medicaments can be selected from the magazine, and a code-reading unit capable of reading the identification code of a medicament, the control unit controlling, on the basis of the prescription signal received, the selection unit in such a manner that the medicament associated with the prescription signal is selected from the magazine, the code-reading unit reads the code of the selected medicament and transmits it to the control unit, whereupon the control unit determines on the basis of the code whether a medicament corresponding to the prescription signal has been selected. The check ensures that it is entirely impossible that a wrong medicament is delivered to a patient.

In particular, the selection unit conveys the selected medicament from the magazine. In accordance with another aspect of the invention, the selection unit releases the selected medicament to a patient when the control unit determines, on the basis of the identification code read, that a medicament corresponding to the prescription signal has been selected.

The automatic dispenser may further comprise a printer printing for instance the patient's name, the medicament and the dosage of the medicament on a label for the medicament to be released.

In accordance with a highly advanced embodiment of the invention, the input unit comprises a data bank wherein various data about indications with corresponding prescriptions of medicaments are stored, as well as for instance data of a patient, the input unit checking according to a predetermined algorithm whether a prescription prescribed for a patient corresponds to the data stored in the data bank. Hence, for drawing up the prescription, the doctor is assisted by the system. Also, unnecessary mistakes can be prevented. More in particular, the input unit produces a signal intended for the doctor when a deviation in the prescription is found during the check carried out by the input unit. In this connection, one may for instance think of the following deviations. The doctor selects a medicament which does not correspond to an indication entered by the doctor. The input unit may also generate a list of possible medicaments when an indication is inputted, with the signal being produced when the doctor does not adopt the first choice of the input unit. Furthermore, a signal can be produced when not the usual strength or dosage of a medicament is inputted. In this manner, it is also possible to draw the doctor's attention to possible interactions with other medicaments prescribed.

The invention also relates to an automatic dispenser suitable for use in a pharmacy system for a dispensing general practitioner as described hereinabove.

BRIEF DESCRIPTION OF THE DRAWINGS

The invention will be further explained which reference to the accompanying drawings. In these drawings.

DETAILED DESCRIPTION OF THE PREFERRED EMBODIMENT

Figure 1:
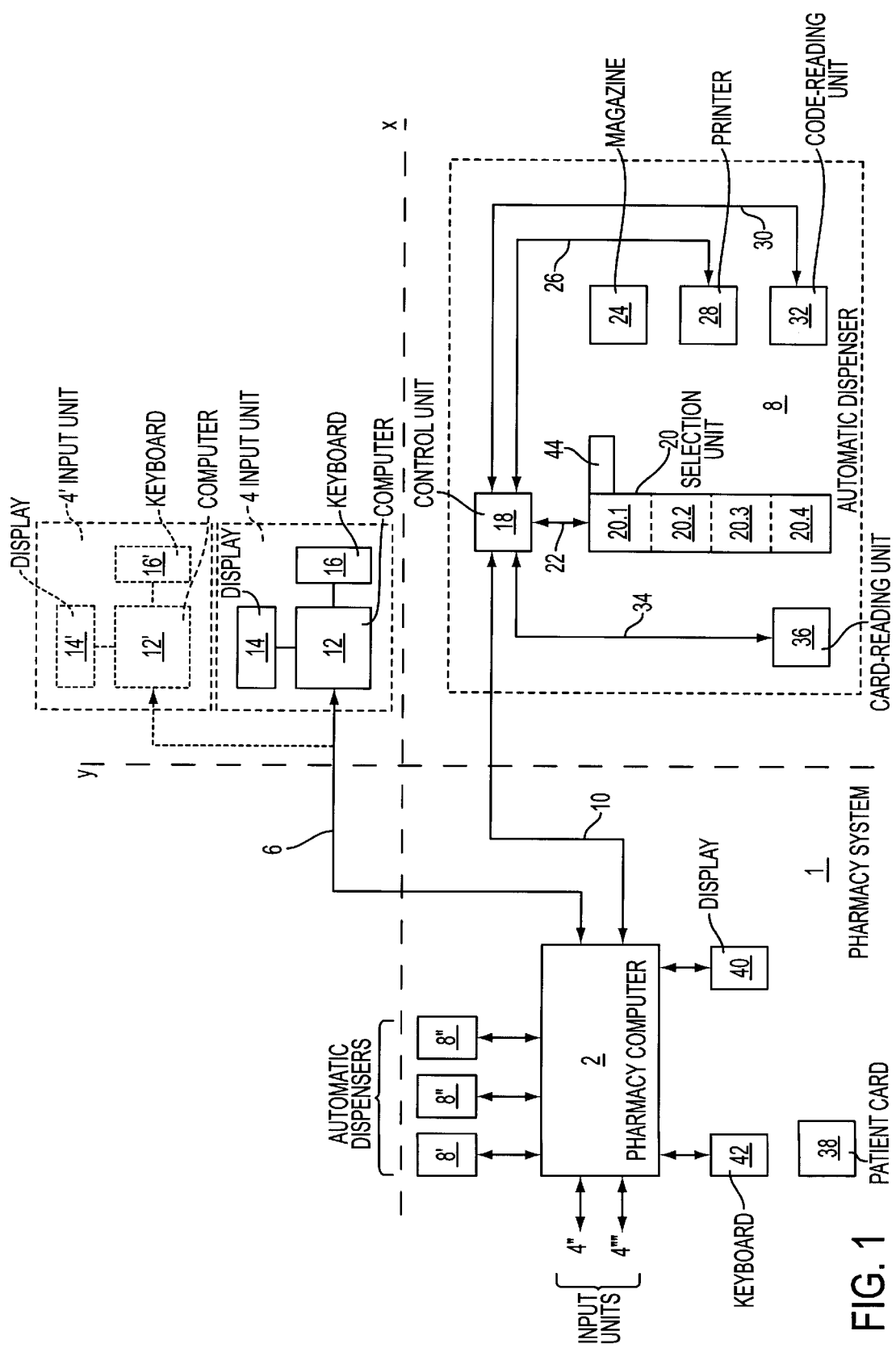
FIG. 1 shows a first possible embodiment of a pharmacy system according to the invention.

In FIG. 1, reference numeral 1 designates a pharmacy system according to the invention. In this example, the pharmacy system comprises a pharmacy computer 2 and an input unit 4, interconnected by means of a data line 6. Here, by means of modems, an existing telephone connection can for instance be used. The system 1 further comprises an automatic dispenser 8, connected with the pharmacy computer 2 by means of a data line 10. Generally, the system will be provided with a number of automatic dispensers connected to the pharmacy computer, in FIG. 1 schematically indicated by 8', 8", 8'", etc. The system may also be provided with a number of input units, schematically indicated by 4", 4"", etc.

In this example, the input unit 4 comprises a computer 12 and a monitor 14 and keyboard 16 connected herewith. The input unit 4 further comprises a data bank wherein various data about indications with associated prescriptions of medicaments are stored, as well as for instance data of a patient, the input unit checking according to a predetermined algorithm whether a prescription prescribed for a patient corresponds to the data stored in the data bank.

In this example, the automatic dispenser comprises a control unit 18 and a selection unit 20, controlled by the control unit 18 by means of line 22. In addition, the automatic dispenser 8 comprises a magazine 24, a code-reading unit 28 connected with the control unit 18 by means of line 26, a printer 32 connected with the control unit 18 by means of line 30, and a code-reading unit 36 connected with the control unit 18 by means of line 34. Furthermore, the system comprises a number of patient cards 38, one of which is shown in FIG. 1. The pharmacy computer 2, comprises a pharmacy data bank wherein various data about indications with corresponding prescriptions of medicaments are stored, as well as for instance data of a patient, the pharmacy computer checking according to a predetermined algorithm whether a prescription received by means of the prescription signal corresponds to the data stored in the pharmacy data bank.

In this example, the pharmacy computer 2 is spatially separated from the input unit 4 and the automatic dispenser. By spatially separated is meant that the pharmacy computer 2 and the input unit 4 can be displaced relative to each other; i.e., the pharmacy computer 2 is accommodated in a different housing from the housing of the input unit 4 and the automatic dispenser 8. Accordingly, in this example, the pharmacy computer is positioned in a different room from the room of the automatic dispenser and the input unit. The pharmacy computer is for instance disposed at and under responsibility of a pharmacist. The input unit 4 is disposed in the surgery of a doctor, while the automatic dispenser 8 is disposed close to the surgery of the doctor, for instance in the same building. The spatial separation referred to is schematically indicated in the Figure by a y-axis. In the Figure, the portion located above an x-axis is brought under the responsibility of the doctor, whereas the portion located below the x-axis is brought under the responsibility of the pharmacist.

The operation of the system is as follows. A prescription generally comprises the name, address and telephone/fax number of the doctor, the personal particulars of the patient, data such as name, strength, amount, and form of administration of the medicament and the use such as frequency of administration and particular information with respect hereto. Such a prescription is drawn up by the doctor as follows. The doctor calls the patient from the data bank of the input unit 4 or from the data bank of the pharmacy computer 2. If the patient's identity is not known in the system, the doctor may enter the identity into the system, if desired. If the input unit comprises a card reader, the identity of a patient may also be entered by means of his patient card. Then via a keyboard 16, the indication (diagnosis) is entered. This indication is then displayed on the monitor 14. After this, the doctor may indicate via the keyboard that he agrees to this.

The system, i.e. the computer 12 in this example, generates a menu with medicaments for the indication given. The medicaments shown in the menu, which are known to be contained in the assortment of the automatic dispenser 8, are displayed so as to be distinguishable from the other medicaments shown. The distinction can for instance be indicated by displaying these medicaments with a particular color or brightness, or to mark them with a label. From this, the doctor selects his choice by means of the keyboard 16. Then, the input unit 4 shows the selected medicament on the screen 14. Also, the input unit 4 checks according to a predetermined algorithm whether the selection of the doctor differs from the first choice shown on the screen 14. If a deviation is present, an audio-visual signal is produced by the input unit. If the doctor then indicates via the keyboard that he still agrees to the prescription, the input unit 2 will incorporate this deviation into the electronic prescription that is yet to be transmitted to the pharmacy computer 2 via data line 6.

The doctor may also decide to choose another medicament, whereupon the above-described procedure is repeated.

After the doctor has thus selected a medicament, the input unit presents, on the basis of information in its data bank, a ready-made prescription for the medicament selected. This prescription comprises the usual strength, usual form of administration, usual amounts in multiple of standard package, and the usual frequency of administration and further texts for a label of the medicament.

If so desired, the doctor may change these usual data, should this be required for the specific case of the relevant patient. The input unit generates an audio-visual signal when the doctor goes outside the dosage limits stored in the data bank of the input unit. If the doctor then indicates by means of the keyboard that he still agrees to this dosage, the input unit 2 will incorporate this deviation into the electronic prescription that is yet to be transmitted to the pharmacy computer 2 via data line 6. However, the doctor may also decide yet to adjust the dosage, whereupon the input unit checks the newly entered data again on the basis of the predetermined algorithm.

For more medicaments, the doctor starts the entire procedure described hereinabove afresh. In the menu, medicaments which are known to cause prohibited interactions with the priorly selected medicaments are marked with for instance a star, color, etc. The medicaments present in the automatic dispenser are again shown in a distinctive manner. If according to the predetermined algorithm relative interactions can be expected on the basis of a selection of the doctor from the medicament list shown, the input unit 4 again generates an audio-visual alarm. If the doctor then indicates via the keyboard 16 that he still agrees to his selection, the input unit 2 will incorporate this deviation into the electronic prescription that is yet to be transmitted to the pharmacy computer 2 via data line 6. However, the doctor may also decide yet to adjust the selection, whereupon the input unit checks the newly entered data again on the basis of the predetermined algorithm.

If the prescription drawn up in accordance with the above-described procedure is definitively found in order by the doctor, the prescription or the prescriptions, optionally in combination with the found deviations, are transmitted on-line to the pharmacy computer 2 via data line 6, whereupon, if required, the received prescription signal is temporarily stored for further processing. The pharmacy computer 2 checks whether the prescription comprises deviations priorly determined by the input unit. If this is the case, in this example, an audio-visual signal is produced by the pharmacy computer 2, permitting a pharmacist to judge the matter personally and, if desired, contact the doctor in question. For this purpose, the relevant prescription is for instance displayed on a screen 40. In consultation with the doctor, the prescription can then be adjusted in the pharmacy computer 2 by the pharmacist and found in order. The pharmacist may also indicate via a keyboard 42 that he yet agrees to the prescription shown. In both last-mentioned cases, the prescription is therefore given an 'OK status'. If the prescription does not comprise any deviations it will also be given an 'OK status'.

Further, the pharmacy computer also subjects the received prescription signal for a patient to a check according to a predetermined algorithm, to make sure that the relevant prescription corresponds to the data stored in the pharmacy data bank. This check for instance comprises, as described with respect to the input unit, a check to make sure that the medicament corresponds to the indication (diagnosis). Moreover, it is checked whether the prescription meets the norms of the usual strength, usual form of administration, usual amounts in multiple of standard package, and the usual frequency of administration and of further texts for a label of the medicament. If no deviations are found, the prescription is given or maintains the 'OK status'.

If a deviation is found here, the pharmacist is also warned by means of an audio-visual signal, enabling a pharmacist to judge the matter personally and, if desired, contact the relevant doctor in question. The relevant prescription is then for instance shown on the screen 40 again. In consultation with the doctor, the prescription can then be adjusted in the pharmacy computer 2 by the pharmacist and found in order. The pharmacist may also indicate via the keyboard 42 that he yet agrees to the prescription shown. In these last-mentioned cases, too, the prescription is given the 'OK status'.

A patient then applies at the automatic dispenser 8 and has his patient card 38 read by the card-reading unit 36. On the patient card, the personal particulars of the patient are stored, inter alia. The card may for instance be a magnetic strip card, but may also be a smart card. The identity code read from the card is supplied to the control unit 18 via line 34. The control unit 18 then transmits this code to the pharmacy computer 2 by means of data line 10. The control unit 18 also transmits an address indicating from which automatic dispenser (8, 8', 8", 8''', etc.) the identity code is derived. Then, the pharmacy computer 2 searches its memory for the prescription associated with the identity code of the patient. If the prescription is found and has an 'OK status', the pharmacy computer provides, via data line 10, a control signal to the relevant automatic dispenser for delivering the medicaments to the relevant patient. For this purpose, on the basis of the address mentioned, the control signal is of course transmitted to that automatic dispenser from which the identity code of the patient originated. After this, all data concerning the prescription that are present in the pharmacy computer 2 have been transmitted to the control unit 18.

In this example, the control signal that is transmitted to the automatic dispenser comprises the complete prescription, including the identity of the patient.

In this example, the magazine 24 of the automatic dispenser 8 is loaded with prepacked medicaments whose package has been provided with a unique identification code for the medicaments contained in the relevant package. In this example, the medicaments are stored in the magazine in a predetermined order. This order is also stored in a memory of the control unit 18.

Upon reception of the control signal, the control unit 18 controls, via line 22, the selection unit 22 so that it selects from the magazine 24 a medicament that is stored in the control signal. For this purpose, the selection unit 20 comprises a schematically shown robot arm 44, which will not be further described in this example.

The medicament in question is gripped by the robot arm 44 and conveyed outside the magazine, for instance to a location 20.1 of the selection unit 20. Of course, it is also possible to select and convey the medicaments with other means. In this connection, one may for instance think of principles used in cigaret machines, wherein a packet of cigarets of a particularly brand can readily be selected by the machine so as to be subsequently conveyed from the magazine of the machine.

The medicament located on the location 20.1 is then carried by the selection unit 20 to a location 20.2. The code-reading unit 28 is disposed relative to the location 20.2 so as to be able to read the identification code present in or on the package of the selected medicament. This code may for instance be a bar code. However, it is also possible that the package is provided with a known series-resonant detection label, with the code-reading unit transmitting an electromagnetic interrogation field and comprising a receiver for detecting a response transmitted by the label, from which response the code can be detected.

Via line 26, the identification code of the medicament, determined by the code-reading unit 28, is transmitted to the control unit 18. The control unit 18 compares this code with the contents of the priorly received control signal to check whether the correct medicament has been selected. If the correct medicament has been selected, the control unit 18 controls, via line 22, the selection unit so that the medicament is conveyed to a location 20.3. Adjacent this location, the printer 32 is located, which is then controlled by the control unit 18 via line 30 so that a label with the desired data thereon is printed for the selected medicament. Then, the label text is provided on the package of the selected medicament through means of the selection unit 20 that are not further described.

After this, the control unit 18 controls the selection unit 20 so as to send the medicament ready for delivery to a location 20.4. The medicament can then be taken from the location 20.4 and, after a check on the legibility of the label text, taken along by the patient. The medicament conveyance from and to the locations 20.1, 20.2, 20.3, and 20.4 can be carried out with means known per se, which will not be further explained here.

If, on the basis of the code selected by the code-reading unit 28, the control unit determines that not the correct medicament has been selected, an alarm is transmitted to the pharmacy computer 2, via line 10, enabling the pharmacist to take further action. Obviously, in that case the medicament is not conveyed to the locations 20.3 and 20.4 for further processing. Instead, the medicament is conveyed to a separate location, not shown, for further investigation.

After delivery of the medicament, the control unit 18 transmits a signal to the pharmacy computer 2. Upon reception of this signal, the pharmacy computer 2 can present, via line 6, data to the computer 12 for possible incorporation thereof into the history of the patient. Possible corrections to the original electronic prescription carried out by the pharmacy computer 2 are stored in the computer 12, provided with a mark.

Further, it is also possible that data concerning the prescription are stored on the patient card 8 by means of code-reading unit 36. This has as an advantage that the history of a patient can always and anywhere be read.

In addition, it is possible that a medicament is not conveyed along the locations 20.1–20.3 for printing, fixing and checking of a label, but that instead, the code-reading unit 28 and/or the printer 32 is conveyed to the medicament.

In accordance with an alternative use of the system according to FIG. 1, the input unit 4 is disposed in a room of an assistant of a doctor. This assistant composes a prescription, as described hereinabove with respect to the doctor. Via the data line 6, the thus obtained prescription is sent to an input unit 4', for instance disposed in the surgery of the doctor and for instance identical to the input unit 4. The arrangement is such that the assistant can send the prescription composed by means of the input unit 4 only to the input unit 4' of the doctor and not directly to the pharmacy computer 2. The doctor checks the prescription together with the stored information, if any, about the deviations mentioned before. After checking, the doctor may definitively approve the prescription by means of the keyboard 16', whereupon the prescription or prescriptions found in order are, if necessary, temporarily stored in a memory or on a hard disk of the computer 12'. On the other hand, it is also possible that the doctor decides to adjust the selection as yet, after which the input unit 4' checks the newly entered data again, on the basis of the predetermined algorithm of the type discussed hereinabove with respect to the input unit 4. If this prescription composed in accordance with the above-described procedure is definitively found in order by the doctor—for instance by means of a command entered via keyboard 16'—the prescription or the prescriptions are, if necessary, temporarily stored in a memory or on a hard disk of the computer 12' of the input unit 4'. Then, a patient goes to the automatic dispenser 8 and has his patient card 38 read by the card-reading unit 36. The further delivery of the medicament is then entirely analogous with the above description.

According to a further variant of the system according to FIG. 1, the prescription signal also comprises information about the address indicating at which automatic dispenser (8, 8', 8", 8'", etc.) the medicament will be collected. Accordingly, the control signal is supplied to the relevant automatic dispenser and stored in a memory of the control unit 18. When a patient goes to the relevant automatic dispenser and has his patient card read out by the card-reading unit 36, the patient's identity is supplied to the control unit 18. The control unit 18 then searches its memory for the control signal associated with the identity of the patient and delivers a medicament, as described hereinabove when the identity of the patient, determined by means of the patient card, corresponds to the patient's identity inputted by means of the input unit. Further, the automatic dispenser may also comprise a printer by means of which information relevant to the patient is printed on paper. The patient can then take along this information together with the medicament.

Figure 2:
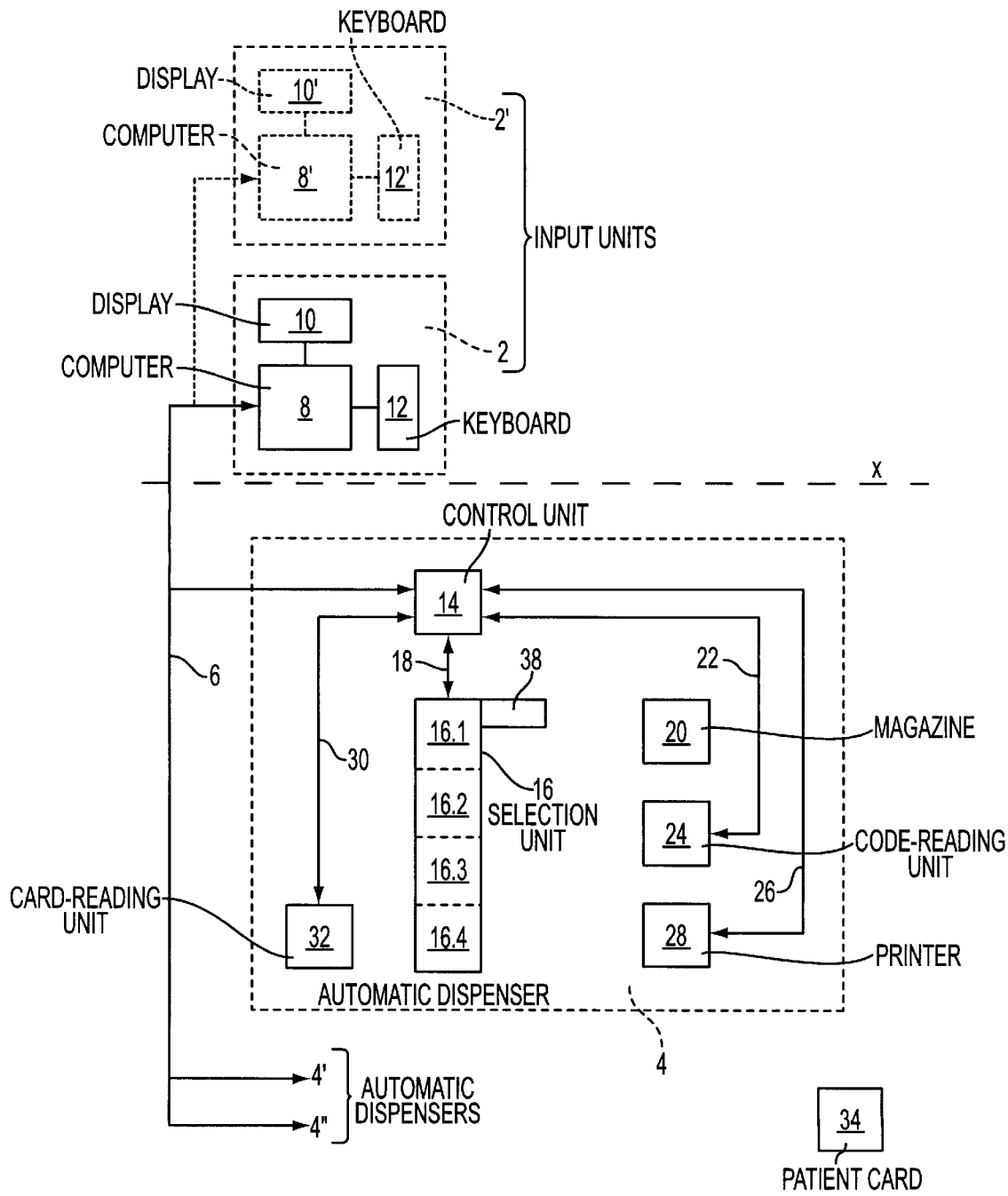
FIG. 2 shows a second possible embodiment of a pharmacy system according to the invention.

In FIG. 2, reference numeral 1 designates a pharmacy system according to the invention, in particular suitable for use at dispensing general practitioners. In this example, the pharmacy system comprises an input unit 2 and an automatic dispenser 4, connected with the input unit 2 by means of a data line 6. In general, the system may comprise a number of automatic dispensers connected to the input unit 2 and in FIG. 1 schematically indicated by 4', 4", 4'", etc.

In this example, the input unit 2 comprises a computer 8 and a monitor 10 and keyboard 12 connected therewith. The input unit 2 further comprises a data bank wherein various data about indications with associated prescriptions of medicaments are stored, as well as for instance data of a patient, the input unit checking according to a predetermined algorithm whether a prescription prescribed for a patient corresponds to the data stored in the data bank.

In this example, the automatic dispenser comprises a control unit 14 and an selection unit 16, controlled by the control unit 14 by means of line 18. In addition, the automatic dispenser 4 comprises a magazine 20, a code-reading unit 24 connected with the control unit 14 by means of line 22, a printer 28 connected with the control unit 14 by means of line 26, and a code-reading unit 32 connected with the control unit 14 by means of line 30. Furthermore, the system comprises a number of patient cards 34, one of which is shown in FIG. 1.

The input unit 2 is disposed in the surgery of a doctor, while the automatic dispenser 4 is disposed close to the surgery of the doctor, for instance in the same building. This spatial separation is schematically indicated in the Figure by an x-axis. In FIG. 2, the portion located above an x-axis is brought under the responsibility of the doctor, whereas the portion located below the x-axis is brought under the responsibility of the doctor or pharmacist. Hence, the automatic dispenser and the input unit are accommodated in housings separated from each other.

The operation of the system is as follows. A prescription generally comprises the name, address and telephone/fax number of the doctor, the personal particulars of the patient, data such as name, strength, amount, and form of administration of the medicament and the use such as frequency of administration and particular information with respect hereto. Such a prescription is composed by the doctor as follows. The doctor calls the patient from the data bank of the input unit 2. If the patient's identity is not known in the system, the doctor may enter this identity into the system, if desired. If the input unit is provided with a card reader, the identity of a patient may also be inputted by means of his patient card. Then, via the keyboard 12, the indication (diagnosis) is entered. This indication is then shown on the monitor 10. After this, the doctor can indicate via the keyboard that he agrees to this.

The system, i.e. the computer 8 in this example, generates a menu with medicaments for the indication given. The medicaments shown in the menu which are known to be contained in the assortment of the automatic dispenser 4, are displayed so as to be distinguishable from the other medicaments shown. The distinction can for instance be indicated by displaying these medicaments with a particular color or brightness, or to mark them with a label. From this, the doctor selects his choice by means of the keyboard 12. The input-unit 2 then shows the selected medicament on the screen 10. The input unit 2 also checks according to a predetermined algorithm whether the selection of the doctor differs from the first choice shown on the screen 10. If a deviation is present, an audio-visual signal is produced by the input unit. If the doctor then indicates by means of the keyboard that he still agrees to the prescription, the input unit 2 will incorporate this deviation into its data bank.

The doctor may also decide to choose another medicament, after which the above-described procedure is repeated.

After the doctor has thus selected a medicament, the input unit presents, on the basis of information in its data bank, a ready-made prescription for the selected medicament. This prescription comprises the usual strength, usual form of administration, usual amounts in multiple of standard package, and the usual frequency of administration and further texts for a label of the medicament.

If so desired, the doctor may change these usual data, should this be required for the specific case of the relevant patient. The input unit generates an audio-visual signal when the doctor goes outside the dosage limits stored in the data bank of the input unit. If the doctor then indicates by means of the keyboard that he still agrees to this dosage, the input unit 2 will incorporate this deviation into the data bank, which in this example is stored on a hard disk of the computer 8. However, the doctor may also decide yet to adjust the dosage, whereupon the input unit checks the newly entered data again, on the basis of the predetermined algorithm.

For more medicaments, the doctor starts the entire above-described procedure afresh. In the menu, medicaments of which it is known that they do not cause any prohibited interactions with the priorly selected medicaments are marked with for instance a star, color, etc. The medicaments present in the automatic dispenser are again shown in a distinctive manner. If according to the predetermined algorithm relative interactions can be expected on the basis of a selection of the doctor from the medicament list shown, the input unit 2 again generates an audio-visual alarm. If the doctor then indicates via the keyboard 12 that he still agrees to his selection, the input unit 2 will again record this deviation in its data bank. However, the doctor may also decide yet to adjust the selection, whereupon the input unit checks the newly entered data again, on the basis of the predetermined algorithm.

If the prescription composed in accordance with the above-described procedure is definitively found in order by the doctor, the prescription or the prescriptions are, if necessary, temporarily stored in a memory or on a hard disk of the computer 8 for further processing.

A patient then goes to the automatic dispenser 4 and has his patient card 34 read out by the card-reading unit 32. On the patient card, the personal particulars of the patient are stored, inter alia. The card can for instance be a magnetic strip card, but may also be a smart card. The identity code read from the card is supplied to the control unit 14 via line 30. The control unit 14 then transmits this code to the input unit 2 by means of data line 6. The control unit 14 also sends an address indicating from which automatic dispenser (4, 4', 4", 4''', etc.) the identity code is derived. The input unit 2 then searches its memory for the stored prescription associated with the identity code of the patient. If the prescription is found, the computer 8 provides, via data line 6, a prescription signal to the relevant automatic dispenser for delivering the medicaments to the relevant patient. For this purpose, on the basis of the address mentioned, the prescription signal is of course sent to that automatic dispenser where the identity code of the patient originated from. After this, all data concerning the prescription that are present in the computer 8 have been transmitted to the control unit 14.

In this example, the prescription signal that is sent to the automatic dispenser comprises the complete prescription, including the patient's identity.

In this example, the magazine 20 of the automatic dispenser 4 is loaded with prepacked medicaments whose package has been provided with a unique identification code for the medicaments contained in the relevant package. In this example, the medicaments are stored in the magazine in a predetermined order. This order is also stored in a memory of the control unit 14.

After reception of the prescription signal, the control unit 14 controls, via line 18, the selection unit 16 so that this selection unit selects from the magazine 20 a medicament stored in the prescription signal. For this purpose, the selection unit 16 is provided with a schematically shown robot arm 38, which will not be further described in this example.

The relevant medicament is gripped by the robot arm 38 and conveyed outside the magazine, for instance to a location 16.1 of the selection unit 16. Of course, it is also possible to select and convey the medicaments with other means. In this connection, one may for instance think of principles used in cigaret machines, wherein a packet of cigarets of a particular brand can readily be selected by the machine so as to be subsequently conveyed from the magazine of the machine.

The medicament located on the location 16.1 is then carried to a location 16.2 by the selection unit 16. The code-reading unit 24 is disposed relative to the location 16.2 so as to be able to read the identification code present in or on the package of the selected medicament. This code may for instance be a bar code. However, it is also possible that the package is provided with a known series-resonant detection label, with the code-reading unit transmitting an electromagnetic interrogation field and comprising a receiver for detecting a response transmitted by the label, from which response the code can be detected.

The identification code of the medicament, determined by the code-reading unit 24, is transmitted to the control unit 14 via line 22. The control unit 14 compares this code with the contents of the priorly received prescription signal to check whether the correct medicament has been selected. If the correct medicament has been selected, the control unit 14 controls, via line 18, the selection unit so that the medicament is conveyed to a location 16.3. Adjacent this location, the printer 28 is located, which is then controlled by the control unit 14 via line 26 so that a label with the desired data thereon is printed for the selected medicament. The label text is then provided on the package of the selected medicament through means of the selection unit 16 not further described.

After this, the control unit 14 controls the selection unit 16 so that the medicament ready for delivery is sent to a location 16.4. The medicament can then be taken from the location 16.4 and, after a check on the legibility of the label text, taken along by the patient. The medicament conveyance from and to the locations 16.1, 16.2, 16.3, and 16.4 can be carried out with means known per se, which will not be further explained here.

If, on the basis of the code selected by the code-reading unit 24, the control unit determines that not the correct medicament has been selected, an alarm is sent to the input unit 2 via line 6, enabling the doctor to take further action. Obviously, in that case the medicament is not conveyed to the locations 16.3 and 16.4 for further processing, Instead, the medicament is conveyed to a separate location, not shown, for further investigation.

After delivery of the medicament the control unit 14 sends a signal to the input unit 2. Then, upon reception of this signal, the computer 8 can store data about the medicament delivered to the patient in the history of the patient.

Further, it is also possible that data concerning the prescription are stored on the patient card 34 by means of code-reading unit 32. This has as advantage that the history of the patient can always and anywhere be read.

In addition, it is possible that a medicament is not conveyed along the locations 16.1–16.3 for printing, fixing and checking a label, but that instead, the code-reading unit 24 and/or the printer 28 is conveyed to the medicament.

It is also possible that a prescription generated by means of the input unit 2 according to the above-described procedure is directly sent, via line 6, to the control unit 14 of the automatic dispenser 4. According to this variant, the prescription is stored together with the identity in the control unit 14. If a patient has his patient card subsequently read by the card-reading unit 32, the data read, including the personal particulars of the patient, are supplied to the control unit 14. The control unit 14 then selects the prescription associated with the identity read in, whereupon the medicament mentioned in the prescription is delivered as described hereinabove.

In accordance with an alternative use of the system according to the invention, the input unit 2 is disposed in a room of an assistant of a doctor. This assistant composes an prescription as described hereinabove with respect to the doctor. Via the data line 6, the thus obtained prescription is sent to an input unit 2', for instance disposed in the surgery of the doctor and for instance identical to the input unit 2 The arrangement is such that the assistant can send the prescription composed by means of the input unit 2 only to the input unit 2' of the doctor and not directly to an automatic dispenser 4, 4', 41". The doctor checks the prescription together with the information, if any, about the deviations mentioned before. After checking, the doctor can definitively approve the prescription by means of the keyboard 12', whereupon the prescription or prescriptions found in order are, if necessary, temporarily stored in a memory or on a hard disk of the computer 8'. On the other hand, it is also possible that the doctor decides to adjust the selection as yet, after which the input unit 2' checks the newly entered data again, on the basis of the predetermined algorithm of the type discussed hereinabove with respect to the input unit 2. If this prescription composed in accordance with the above-described procedure is definitively found in order by the doctor—for instance by means of a command entered via the keyboard 12'—the prescription or the prescriptions are, if necessary, temporarily stored in a memory or on a hard disk of the computer 8' of the input unit 2'. A patient then goes to the delivery unit 4 and has his patient card 34 read out by the card-reading unit 32. The further delivery of the medicament is then entirely analogous with the above description, the difference being that the control unit 14 transmits the identity code read from the patient card to the input-unit 2' by means of data line 6. The input unit 2' then searches its memory for the stored prescription associated with the identity code of the patient. If the prescription is found, the computer 8' provides, via data line 6 of the relevant automatic dispenser, a prescription signal for delivering the medicaments to the relevant patient.

Further, the automatic dispenser may also comprise a printer by means of which the information relevant to the patient is printed on paper. The patient can then take along this information together with the medicament.

These and other variations, readily apparent to a skilled person, are considered to fall within the purview of the invention.

What is claimed is:

1. A method of prescribing and delivering medicaments to a patient, said method comprising the steps of:

a) providing an interactive medicament suggesting, prescribing, and delivering system for prescribing and delivering medicaments to a patient, said system comprising at least one input unit and at least one automatic dispenser which can be loaded with medicaments, wherein the input unit comprises a data bank in which is stored data of a patient as well as suggested prescription data, said suggested prescription data comprising indications and corresponding suggested prescriptions for medicaments for treating a patient presenting with such indications, whereby the prescription for a medicament for a patient can be selected from a list of suggested medicaments provided by the input unit and entered into the input unit together with the identity of the patient, the input unit checking according to a predetermined algorithm whether a selected prescription prescribed for a patient corresponds to the data stored in the data bank and the input unit generating a prescription signal corresponding to the prescription selected and entered, wherein the system further comprises a pharmacy computer that is remote from and coupled to the input unit, said pharmacy computer further processing the prescription signal received from the input unit and generating a control signal corresponding to the prescription, the at least one automatic dispenser then dispensing the prescribed medicament under the control of the control signal generated by the pharmacy computer, whereby the doctor can interactively select and prescribe a medicament for a patient selected from said list of suggested medicaments at a first location and the patient can automatically receive the medicament at another, remote location;

b) having a doctor at said first location select a medicament for the patient from the list of suggested medicaments and enter the prescription for a medicament for the patient, together with the identity of the patient, into one of said at least one input unit;

c) having the input unit check according to a predetermined algorithm whether the prescription prescribed for the patient corresponds to the data stored in the data bank and generate a prescription signal corresponding to the prescription that has been entered;

d) having said pharmacy computer, under the independent control of a pharmacist, process the prescription signal received from the input unit and generate a control signal corresponding to the prescription; and e) having said at least one automatic dispenser dispense the prescribed medicament based on the control signal generated by the pharmacy computer.

2. A method of prescribing and delivering medicaments to a patient, said method comprising the steps of:

a) providing a medicament prescribing and delivering system for prescribing and delivering medicaments to a patient, said system comprising at least one input unit which provides a list of suggested medicaments for treating a patient presenting with particular indications and with which a doctor selects and enters a prescription for a medicament for a patient and at least one automatic dispenser which can be loaded with medicaments, wherein the prescription for a medicament for a patient can be entered into the input unit together with identity of the patient, wherein the input unit generates a prescription signal corresponding to the prescription entered, the system further comprising a pharmacy computer remote from and coupled to the input unit, the pharmacy computer further processing the prescription signal received from the input unit and generating a control signal corresponding to the prescription, the system further comprising means for determining the identity of a patient, the system comparing the determined identity with the identity of a patient associated with a prescription entered, the at least one automatic dispenser then dispensing the prescribed medicament under the control of the control signal generated by the pharmacy computer, whereby the doctor can prescribe a medicament for a patient at one location and the patient can automatically receive the medicament at another, remote location;

b) having a doctor at said first location select and enter a prescription for a medicament for the patient, together with the identity of the patient, into one of said at least one input unit;

c) having the input unit check according to a predetermined algorithm whether the prescription prescribed for the patient corresponds to the data stored in the data bank and generate a prescription signal corresponding to the prescription that has been entered;

d) having said pharmacy computer, under the independent control of a pharmacist, process the prescription signal received from the input unit and generate a control signal corresponding to the prescription;

e) determining the identity of a patient with said means for determining the identity of a patient and comparing the determined identity with the identity of a patient associated with the prescription entered by the doctor; and f) having said at least one automatic dispenser dispense the prescribed medicament based on the control signal generated by the pharmacy computer.

* * * * *